(12) United States Patent
Byszewski

(10) Patent No.: US 6,517,700 B2
(45) Date of Patent: Feb. 11, 2003

(54) PROCESS FOR THE REMOVAL OF HEAT STABLE AMINE SALTS

(76) Inventor: Carolyn H. Byszewski, 1, Old Stone La., Whippany, NJ (US) 07981

(*) Notice: Subject to any disclaimer, the term of this patent is extended or adjusted under 35 U.S.C. 154(b) by 32 days.

(21) Appl. No.: 09/848,221

(22) Filed: May 4, 2001

(65) Prior Publication Data
US 2002/0020625 A1 Feb. 21, 2002

Related U.S. Application Data

(60) Provisional application No. 60/201,373, filed on May 2, 2000.

(51) Int. Cl.⁷ .......................... B01D 61/42; B01D 61/44
(52) U.S. Cl. ........................ 205/431; 204/530; 204/534
(58) Field of Search ........................ 205/431; 204/530, 204/534

(56) References Cited

U.S. PATENT DOCUMENTS 5,292,407 A * 3/1994 Roy et al. .................... 205/431

* cited by examiner

Primary Examiner—Arun S. Phasge (57) ABSTRACT

A process is disclosed for removing heat stable amine salts using an electrodialysis process. The process of the present invention can be used to reduce the level of heat stable salts in a lean solvent stream in an acid gas removal process. A base is added to the electrodialysis unit in order to permit the recovery of the heat stable amine salts as salts corresponding to the base added. The purified amine solution can be used again to remove acid gases from a gas stream.

16 Claims, 3 Drawing Sheets

PROCESS FOR THE REMOVAL OF HEAT STABLE AMINE SALTS

This application claims the benefit of Provisional application Ser. No. 60/201,373, filed May 2, 2000.

FIELD OF THE INVENTION

The present invention relates to the removal of heat stable amine salts from liquid streams. More specifically, the present invention relates to processes for 1, converting an amine in salt form to an amine in free base form and 2, removing the anion of the heat stable amine salt as a salt of the associated base that has been added to a modified electrodialysis zone.

BACKGROUND OF THE INVENTION

A wide variety of absorption processes have been proposed for removing acid gases such as, for example, carbon dioxide, hydrogen sulphide, sulphur dioxide, sulphur trioxide, carbon disulphide, hydrogen cyanide, and carbonyl sulphide from process gas streams using absorbents comprising amines.

Such absorption processes typically involve passing the process gas stream containing one or more of the acid gases to an absorption zone wherein it is contacted with a lean solvent comprising the amine absorbent. A product gas stream, depleted in the acid gases relative to the process gas stream, is withdrawn from the absorption zone as a product. A rich solvent stream comprising the amine absorbent and the absorbed acid gases is also withdrawn from the absorption zone and passed to a regeneration zone, e.g. a stripping column, wherein the absorbed acid gases are desorbed from the solvent to provide a tail gas stream comprising the acid gases and the lean solvent stream herein before described.

A common problem in such acid gas absorption processes is that heat stable salts of the amine are often formed during one or both of the absorption and regeneration steps as a by-product. Heat stable salts can be formed, for example, when strong acids such as hydrochloric acid or sulphuric acid are present in the process gas.

Heat stable salts can also be formed when sulphite anions are oxidised to sulphate anions in SO2 amine recovery processes. Typical ions which form heat stable salts, i.e., heat stable anions, include, for example, sulphate anions, thiosulphate anions, polythionate anions, thiocyanate anions, acetate anions, formate anions, nitrate anions, chloride anions, oxylate ions and in addition for amines suitable for $H_2S$ and $CO_2$ scrubbing, sulphite anions. Heat stable salts generally do not have absorption capacity for the acid gases and are not regenerable under the conditions of the process. Therefore, the level of heat stable salts needs to be controlled in order to retain an adequate degree of absorption capacity for the acid gases.

Electrodialysis has been proposed as a method for removing heat stable salts from amine containing streams. In a typical electrodialysis process, (ref U.S. Pat. No. 5,910,611) caustic, e.g., sodium hydroxide, is added to the stream containing the heat stable amine salt in order to dissociate the heat stable anion from the heat stable salt and provide an amine in free base form and a simple heat stable salt, e.g., sodium sulfate. The simple salt is then separated by conventional electrodialysis wherein the charged ions permeate through anion- and cation-selective membranes. The amine, which is non-ionic, does not permeate through the membranes and is discharged from the electrodialysis zone as a product. Often, conventional electrodialysis processes operate in a batch mode wherein the process streams are recirculated until the desired amount of heat stable salts is removed.

Certain problems can result from the use of electrodialysis processes such as described above. For example, since the amine product from the electrodialysis zone is provided in free base form, it can have excessive volatility which can lead to solvent losses during absorption. In addition, when the process is a batch process, the pH and ionic strength within the compartments of the electrolysis zone vary with the discontinuous operation. As a result, the membranes in the electrodialysis zone often experience shrinking and swelling and, ultimately, are subject to mechanical failure. Moreover, to the extent that the amine is not converted to free base form in the caustic treatment step, there can be substantial losses of the amine due to permeation through the membranes in the electrodialysis zone. In addition, there can be significant losses through the membranes as a result of osmostic forces in the conventional electrodialysis process.

An alternative electrodialysis process (U.S. Pat. No. 5,292,407) achieves the removal of the heat stable anion by substituting the heat stable anion with a regenerable non-heat stable anion in a modified electrodialysis zone. In this process, the regenerable anion is introduced into the electrodialysis stack as an acid, such as sulfurous acid, in the case of an $SO_2$ scrubbing process. Neutralizing the heat stable amine salt with a base in order to generate an amine in free base form is not required in this case. Amine losses are significantly reduced. This process suffers from the disadvantage that the regenerable anion must be introduced as an acid with the resultant low pH and associated corrosion or as a salt such as sodium bisulphite, or sodium carbonate. These salts are typically sold as solids implying that they must be mixed and dissolved in addition to often containing significant quantity of impurities. If the regenerable anion is introduced as an acid, then the materials of construction must be chosen such that they are resistant to the low pH environment. In acid form, the regenerable anions often possess significant vapor pressure, resulting in operational difficulties and process hazards in the case of $SO_2$ or $H_2S$. The waste stream will also be composed of acidic species of the non-regenerable acid species, and in most instance would require neutralization before being disposed of.

SUMMARY OF THE INVENTION

In accordance with the present invention, processes are provided which utilize a modified electrodialysis zone in order to convert heat stable amine salts in an amine solution to salts of a base other than the amine in which they were originally associated with and amine in free base form. The process of the present invention can provide a high degree of recovery of the amine in the electrodialysis zone, requires the addition of a base such as caustic and can be highly integrated with acid gas-absorption process. In an alternative embodiment, the addition of caustic can be eliminated by the utilization of bi-polar membranes (water splitting) in which $OH^-$ and $H^+$ ions are generated by dissociation of water molecules.

More specifically, the present invention provides a process for converting heat stable amine salts to free base amine and non-amine salts which comprises:

(a) passing a feedstream comprising an amine in salt form having heat stable anions associated therewith to an electrodialysis zone having a cathode compartment, an anode compartment and at least one repeat unit comprising a base or anion source compartment disposed between the cathode compartment and the anode compartment, a product compartment disposed between the base feed compartment and the anode compartment, a feed compartment disposed between the product compartment and the anode compartment, and a salt compartment disposed between the feed compartment and the anode compartment, said regenerated solvent stream being passed to the feed compartment;

(b) passing a base stream comprising a base such as caustic or equivalent base to the base compartment;

(c) passing a direct current potential transversely across each compartment, said current being effective to cause: (1) amine cations to dissociate from the heat stable amine salts in the feed compartment and pass into the product compartment and be neutralized into its free base form; (2) hydroxide or equivalent anions to be dissociated in the base compartment and pass into the product compartment; and (3) heat stable anions to dissociate from the heat stable amine salts in the feed compartment and pass into the salt compartment; and (4) base cations to dissociate in the base compartment and pass into the salt compartment; and (d) discharging from the product compartment a product stream comprising an amine in salt form having at least a portion of the amine in free base form.

A second embodiment of the same invention which also provides a process for converting heat stable amine salts to free base amine or regenerable amine salts and non-amine salts which comprises:

(a) passing a feedstream comprising an amine in salt form having heat stable anions associated therewith to an electrodialysis zone having a cathode compartment, an anode compartment and at least one repeat unit comprising a anion source compartment disposed between the cathode compartment and the anode compartment, a combined feed and product compartment disposed between the base feed compartment and the anode compartment, and a waste compartment disposed between the combined feed-product compartment and the anode compartment, said regenerated solvent stream being passed to the feed-product compartment;

(b) passing a base stream, or an acid or salt with a regenerable anion, such as caustic in the case of a base or sodium carbonate in the case of a salt with a regenerable anion to the anion source compartment;

(c) passing a direct current potential transversely across each compartment, said current being effective to cause: (1) amine cations to dissociate from the heat stable amine salts in the combined feed and product compartment and be neutralized to its free base form; or into a regenerable form (2) hydroxide or equivalent anions to be dissociated in the anion source compartment and pass into the combine feed and product compartment; and (3)heat stable anions to dissociate from the heat stable amine salts in the feed-product compartment and pass into the waste compartment; and (4) base, acid or salt cations to dissociate in the anion source compartment and pass into the waste compartment; and (d) discharging from the feed-product compartment a product stream comprising an amine in salt form having at least a portion of the amine in free base form or in a regenerable form. A third embodiment of the same invention which also provides a process for converting heat stable amine salts to free base amine and the corresponding acid of the heat stable anions comprises:

(a) passing a feedstream comprising an amine in salt form having heat stable anions associated therewith to an electrodialysis zone having a cathode compartment, an anode compartment and at least one repeat unit comprising a waste (concentrate) feed compartment disposed between the cathode compartment and the anode compartment, a combined feed and product compartment disposed between the waste compartment and the anode compartment, said regenerated solvent stream being passed to the feed-product compartment;

(b) passing a direct current potential transversely across each compartment, said current being effective to cause: (1) amine cations to dissociate from the heat stable amine salts in the combined feed and product compartment and be neutralized to its free base form by hydroxide anions; (2) hydroxide or equivalent anions to be produced in the bi-polar membranes and pass into the combine feed and product compartment; and (3) heat stable anions to dissociate from the heat stable amine salts in the feed-product compartment and pass into the waste compartment; and (4) protons to be generated in the bi-polar membranes and pass into the waste compartment; and (c) discharging from the feed-product compartment a product stream comprising an amine in salt form having at least a portion of the amine in free base form.

DETAILED DESCRIPTION OF THE INVENTION

Feedstreams suitable for use in accordance with the present invention generally include any liquid stream comprising an amine in a salt form having heat stable anions associated therewith. Typically, the feedstreams are aqueous and also comprise at least in part an amine in free base form. The concentration of the heat stable salts is typically from about 0.1 to 25 weight percent based on the total feedstream. In hydrogen sulfide and carbon dioxide acid gas absorption processes, for example, the concentration of heat stable amine salts is often from about 1 to 5 weight percent. In sulfur dioxide acid gas absorption processes, the concentration of heat stable amine salts is often from about 1 to 15 weight percent. The concentration of amine in free base form is typically from about 5 to 60 weight percent, more typically from 20 to 50 weight percent. The concentration of water, when present, typically comprises the balance of the feedstream, and is preferably, from about 30 to 95 weight percent, and, more preferably from about 40 to 70 weight percent, based on the total feedstream. It is not uncommon for the feedstreams to comprise small amounts, e.g., less than about 2 weight percent, of other ingredients such as, for examples, antifoams or antioxidants.

The source of the feedstream is typically from the solvent circulation loop of an acid gas absorption process. Often, the feedstream comprises a slip stream of the lean solvent stream, i.e. regenerated solvent, from the steam stripping column, of an acid gas absorption process, such as described above. However it is to be understood that the source of the feedstream is not a critical aspect of the present invention. In addition, the particular acid gas being absorbed in the acid gas absorption process is not a critical aspect of the present invention. Typical acid gases include hydrogen sulfide, carbon dioxide and sulfur dioxide. When hydrogen sulfide is present in the process gas stream, its concentration typically ranges from about 10 to 50,000 parts per million volume ("ppmv") or even up to 30 volume percent or more. When carbon dioxide is present in the process gas stream, its concentration typically ranges from about 2 to 30 volume percent, although levels of carbon dioxide as high as about 90 volume percent or more are not uncommon. When sulfur oxides are present in the gas stream, i.e. sulfur dioxide and/or sulfur trioxide, their total concentration typically ranges from about 500 ppmv to 50 volume percent, although levels as high as 70 volume percent or more are possible. The process gas streams typically comprises other ingredients such as, for example nitrogen, water, oxygen, light hydrocarbons, and sulfur derivatives of light hydrocarbons, e.g., mercaptans. Suitable amines include, for example aliphatic, aromatic, heterocyclic amines and amides. Typical alkanol amines suitable for use in accordance with the present invention include monoethanolamine, diethanolamine, triethanolamine and methyldiethanolamine, for example. Typical alkyleneamines include for example, ethylene diamine and alkyl derivatives thereof. Typical aromatic amines include, for example aniline and xylidine. Typical heterocyclic amines include, for example, piperazine and derivatives thereof. Typical amides, include piperazinone.

Heat stable salts often form during absorption or regeneration in acid gas absorption processes. As used herein, the term "heat stable salts" means any amine salt which is not regenerated under the regeneration conditions of the process. For example, typical conditions for regenerating the amine include steam stripping in a distillation column at a temperature of from about 75° C. to 160° C. and at a pressure of about 0.2 to 3 atmospheres. Heat stable salts are also known to those skilled in the art as those salts whose anions correspond to nonvolatile or strong acids relative to the strength of the acid gases being regenerably absorbed. Those skilled in the art can determine which anions can form heat stable salts depending on the particular amine and acid gas. Typical ions which form heat stable salts, i.e. heat stable anions, include for example, sulfate anions, nitrate anions, thiosulfate anions, thiocyanate anions, halide anions, nitrite anions, polythionate anions, acetate anions, formate anions, oxylate anions and mixtures thereof. Sulfite anions, which are heat regenerable anions can be heat stable, for example, when present in a hydrogen sulfide or carbon dioxide absorption process.

In accordance with the present invention, a modified electrodialysis zone is utilized to convert an amine in a salt form having heat stable anions (such as described above) associated therewith to an amine in free base form. Typical bases which can be utilized as a source of the neutralizing hydroxide anion include sodium hydroxide and potassium hydroxide. A bi-polar membrane as described in FIG. 4 can be substituted for a source of base.

The conversion of heat stable anions is achieved by modifying the arrangement of the compartments in the electrodialysis zone in order to permit amine cations to pass into a compartment containing a suitable base in order to convert the amine into its free base form, referred to as the four-loop process. Alternatively this conversion reaction can occur in the feed compartment without having to transport the amine across a membrane, referred to the three loop process. In the three loop process, the conversion in the feed compartment need only be to an amine in free base form or to an amine salt that is thermally regenerable. For both the three and four process the base or anion source compartment can be eliminated by the utilization of bi-polar membranes.

In the four loop variation the electrodialysis zone comprises a cathode compartment which attracts cations, and anode compartment which attracts anions and at least one repeat unit which contains a base compartment, a product compartment, a feed compartment and a salt compartment. The base compartment is disposed between the cathode compartment and the anode compartment. The product compartment is disposed between the base compartment and the anode compartment. The feed compartment is disposed between the product compartment and the anode compartment. The salt compartment is disposed between the feed compartment and the anode compartment. Alternatively, in the three-loop process, the product and feed compartments can be combined into a single compartment.

In the four-loop configuration each compartment in the repeat unit is separated by a membrane. The base compartment and product compartment are separated by an anionic selective membrane. The product compartment and the feed compartment are separated by a cationic selective membrane. The feed compartment and the salt compartment are separated by an anionic selective membrane. The salt compartment and the base compartment of an adjacent repeat unit are separated by a cationic selective membrane.

In the three loop configuration the anion source compartment and the combined product and feed compartments are separated by an anion selective membrane. The combined product and feed compartments and the salt compartments are separated by an anion selective membrane. The waste compartment and the anion source compartment of an adjacent repeat unit are separated by a cationic selective membrane.

As used herein, the term "cationic selective membrane" means a membrane which will selectively permeate cations over anions. As used herein, the term "anionic selective membrane" means a membrane which will selectively permeate anions over cations. In general, details concerning such membranes are known in the art. Any suitable or conventional cationic ion exchange membranes and anionic ion exchange membranes can be used in the electrodialysis cell. However, preferred membranes include those which are polyvinylchloride-based. Examples of preferred cationic membranes include Neosepta CM2 and CMX membranes available from Tokuyama Soda Co. Ltd. Examples of anionic selective membranes include Neosepta AM-3 and AM-X membranes also available from Tokuyama Soda Co. Ltd.

Typically the electrodialysis zone will contain from about 10 to 500 repeat units, and preferably will contain from about 40 to 200 repeat units. The process streams generally flow through the compartments in a co-current direction relative to each other. Also the inlets and outlets of common compartments, e.g., product compartments, are typically connected by a common manifold system. Further details concerning operating conditions and the design of electrodialysis zones are known to those skilled in the art.

In the four-loop variation the operation of the electrodialysis zone, the feedstream is passed into the feed compartment wherein amine cations dissociate from the heat stable anions. The amine cations permeate through the cationic selective membrane to the product compartment. The heat stable anions permeate through the anionic selective membrane to the salt compartment. A feed effluent stream, having substantially the same composition as the feedstream except for a reduced concentration of heat stable salts, is discharged from the feed compartment.

A base stream comprising a base which will not dissociate into a heat regenerable anion is introduced to the base compartment, wherein the cation of the base dissociates and permeates through the cationic selective membrane to the adjacent salt compartment. The base anions, e.g. hydroxide, permeates through the anionic selective membrane and pass into the product compartment. Typical bases include alkali metal oxides and hydroxides, alkaline earth oxides and hydroxides and metal oxides and hydroxides. Examples of bases include, sodium oxide or hydroxide and potassium oxide or hydroxide, beryllium hydroxide and zinc hydroxide. Mixtures of bases can be used.

Figure 4:
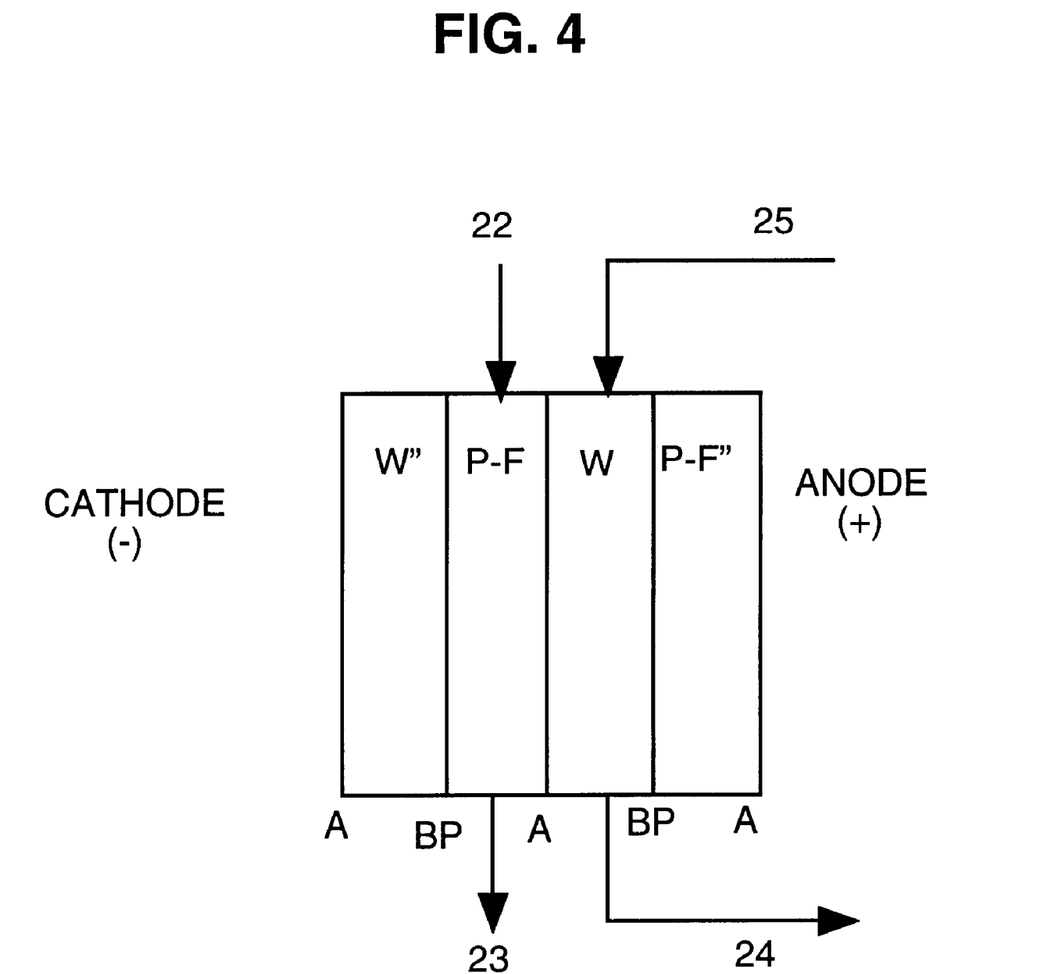
FIG. 4 illustrates a process flow diagram in accordance with the third variation of the present invention wherein a heat stable amine salt is converted into free base amine and the associated acid of the non-regenerable anion. In this embodiment no base feed is required and the base circulation loop contained in FIG. 1 is eliminated.

The introduction of a base or an acid or salt having a regenerable anion is not required when the third embodiment as illustrated in FIG. 4, is employed. The bi-polar membranes otherwise known as water splitting membranes serves to generate in-situe hydroxyl anions. The other product of splitting water is a proton which will combine with the heat stable anion in the waste compartment to form the corresponding acid of the heat stable anion (eg. the sulfate anion will react with the proton to form sulfuric acid). In all references to the waste stream hereinafter it is understood that references to the salt of the heat stable anion as generated in the first two embodiments will be the acid of the heat stable anion when the third embodiment is utilized or when an acid with a regenerable anion is feed into the anion source compartment. In the third embodiment, no base or other source of anions is required, as the base is generated in situe by the bi-polar membranes.

A product stream comprising the amine in a free base form or in a non-heat stable salt form (three loop variation with regenerable anion being feed to the anion source loop), which may contain amine with heat stable and non-heat stable salts, is discharged from the product compartment. The product stream can be re-introduced into the acid gas recovery process, where the free base amine or amine in with non-heat stable salt will serve to lower the overall level of heat stable salts in the circulating amine solution.

A salt or acid stream comprising the salt or acid of the heat stable anion is discharged from the salt compartment. Typical salts of the heat stable anions include, for example, alkali metal sulfates, alkali metal halides, alkali metal acetates, alkali metal thiocyanates, alkali metal thiosulfates, alkali metal nitrates and nitrites, alkaline earth sulfates, alkaline earth halides, alkaline earth acetates, alkaline earth thiocyanates, alkaline earth thiosulfates, alkaline earth nitrates and nitrites and mixtures thereof. Preferred salts of heat stable anions include sodium sulfate, sodium chloride, sodium acetate, sodium thiocyanate, and sodium thiosulfate.

With the third embodiment the acid of the heat stable anions are produced if an acid is utilized as the source of regenerable anions. Preferably the salts and acids are soluble in the said stream and do not precipitate out of solution. Such precipitation could adversely affect the operation of the electrodialysis zone. A carrier stream, preferably an aqueous carrier, is introduced to the salt compartment in order to control the flow rate and the concentration of the salt in the salt stream or acid in the waste stream. The waste stream can be removed from the process as a product. The feedstream and product stream can be introduced to the electrodialysis zone on a once through basis or on a recycle basis. When the electrodialysis zone is operated on a recycle basis, a portion of the feed effluent stream and the base effluent stream is recycled back to the feed compartment and the base compartment, respectively. Methods of recycling such streams are generally known to those skilled in the art. Typically, however, holding tanks are employed whereby the feedstream and base stream are introduced to their respective holding tanks. By operating in this fashion, it is possible to maintain essentially any desired flow rates within the compartments in the electrodialysis zone even though the actual flow rates of the feedstream and base stream to the holding tanks may be substantially lower. Effluent streams are then withdrawn from the holding tanks at flow rates, which are essentially equivalent to the flow rates of the feedstream in order to maintain steady state concentrations and volumes.

In accordance with the present invention, it is possible to maintain the level of heat stable salts in the lean solvent feed to an absorption zone of an acid gas absorption process at a level low enough to not substantially interfere with the absorption of the acid gas.

When the absorbent comprises a monoamine, such as for the absorption of hydrogen sulfide and carbon dioxide or an amide for the absorption of sulfur dioxide, the level of heat stable salts in the regenerated absorbent is preferably less than about 0.25 equivalent of heat stable salt per mole of amine or amide, and more preferably less than about 0.1 equivalent per mole of amine.

When the absorbent comprises a diamine, such as for sulfur dioxide, the level of heat stable salts in the regenerated absorbent is typically less than about 1 equivalent of heat stable salt per mole of diamine, preferably less than about 0.8 equivalent per mole of diamine. For certain special applications, the level of heat stable salts is maintained in the range of 0.5 to 0.9 equivalents per mole or less (ref. U.S. Pat. No. 5,019,361).

Typically, the recovery of amine is at least 80 percent, preferably at least 90 percent and most preferably at least 99 percent. Without being bound to any theory, it is believed that the high recovery is due to the arrangement of the compartments within the electrodialysis zone. In the present invention, the amine cations are substantially only able to permeate through the cationic selective membrane between the feed and product compartments. Since the base or anion source compartment is separated from the product compartment and the combined feed-product compartment in the alternative embodiment, by an anionic selective membrane, very little amine cation, e.g. typically less than about 2 percent, is allowed to permeate to the base or anion source compartment. In addition the free base amine, being of neutral charge, is not influenced by the electric field in the electrodialysis zone, and thus does not tend to permeate from one compartment to another. The free base amine can permeate by osmotic diffusion, but the losses of such to the base or anion source and salt or waste streams can be kept at a minimum by not operating the feedstream and product stream or the combined feedstream and product stream in the alternative embodiment in a recycle mode, or by minimizing the rate of recycle, thus minimizing the concentration of free base amine in these streams.

FIGS. 1, 2, 3 and 4 illustrates a process flow diagram in accordance with the present invention. The process flow diagram is provided for illustrative purposes and are not intended to limit the scope of the claims which follow. Those skilled in the art will recognize that the process flow diagram does not illustrate various common pieces of process equipment such as, for example, heat exchangers, pumps, compressors, distillation columns, heaters, process control systems and the like.

FIG. 1

Figure 1:
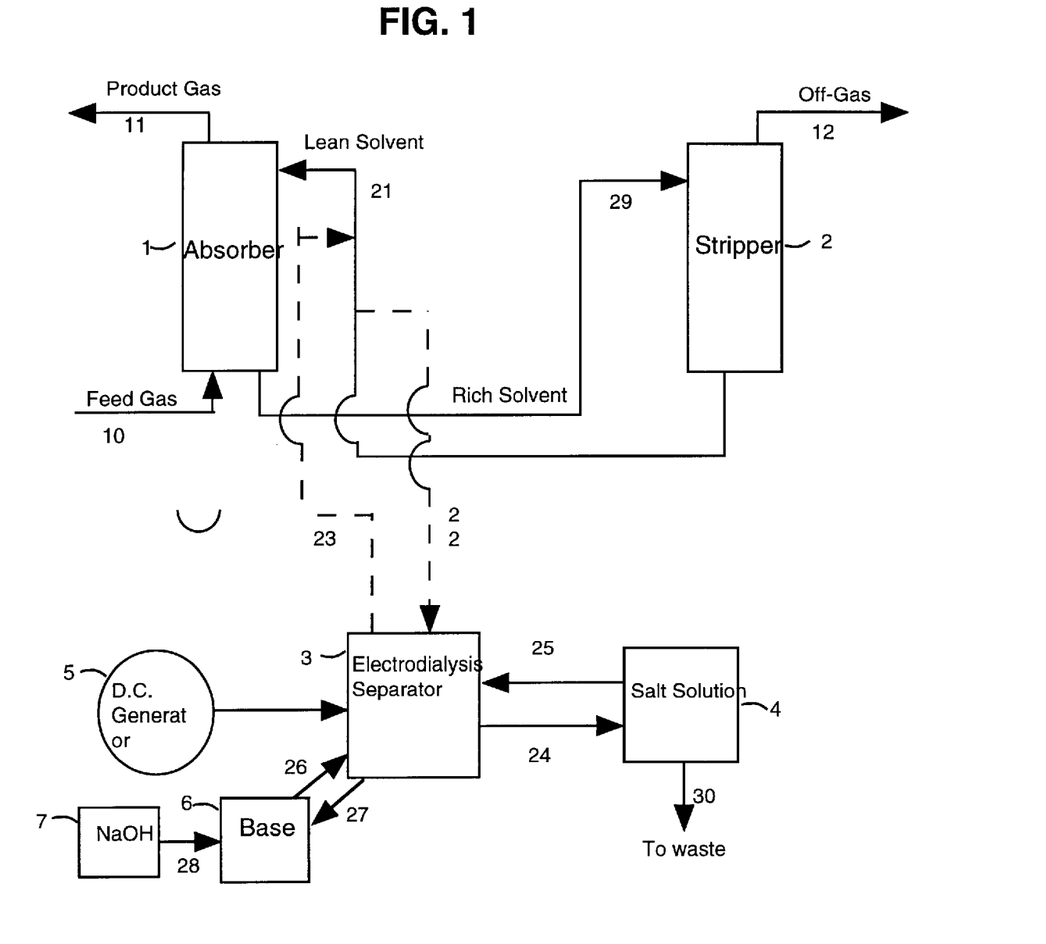
FIG. 1 illustrates a process flow diagram in which an electrodialysis unit is utilized in the context of a gas treating process to remove heat stable salts.

FIG. 1 illustrates an aspect of the invention where a heat stable amine salt, i.e. sulfate salt is converted to a free base amine in the electrodialysis zone.

For example a process gas comprised of hydrogen sulfide, hydrochloric acid with the balance comprising water vapor, methane, ethane and nitrogen is introduced into the process via line 10 and passed into the absorption zone 1. In the absorption zone, the feed process stream is contacted with a lean solvent stream via line 21, the source of which is defined as being comprised of diethanolamine, with the balance being mostly water. Absorption in zone 1 is maintained at temperature of 20° C. to 60° C. and a pressure of 1 atmosphere to 150 atmospheres and comprises a packed tower or spray scrubber, the details of which are known to those skilled in the art. Other types of absorption apparatus could be utilized, as it is not critical to the present invention. During absorption of the hydrogen sulfide, heat stable salts of amine, i.e. having chloride anions associated therewith, are formed.

A product gas stream at least partially depleted in hydrogen sulfide relative to the feed gas stream is discharged from absorption zone 1 via line 11.

A rich solvent stream comprising absorbed hydrogen sulfide and the amine is discharged from absorption zone 1 via line 29, and passed to a regeneration zone 2. During regeneration, hydrogen sulfide is liberated from the absorbent. Regeneration zone 2 is a distillation column operated under steam stripping conditions at a temperature of 75° C. to 150° C. and a pressure of 1 atmosphere to 2 atmospheres, the details of which are known to those skilled in the art. The particular method and apparatus for regeneration is not critical to the present invention. It is common for heat stable salts to form in the regeneration zone as well.

A regeneration overhead stream comprising hydrogen sulfide and water is discharged from regeneration zone 2 via line 12. Regenerated amine or lean solvent is discharged from zone 2 via stream 21.

A slipstream is taken from the lean amine stream, line 21 and introduced into the electrodialysis device (stream 22). The amine is returned to the process at least partially depleted in amine heat stable salts via line 23. Caustic solution is added to a base recirculation tank via line 28. Base is circulated into the electrodialysis zone via lines 27 and 26. Salt solution is recirculated into the electrodialysis zone via lines 24 and 25. Waste products are withdrawn from the salt circulation loop via line 30. Recirculation of amine, base and salt solution is not critical for this invention. In the design and operation of the electrodialysis stack one may choose to utilize recirculation or a once through approach.

Figure 2:
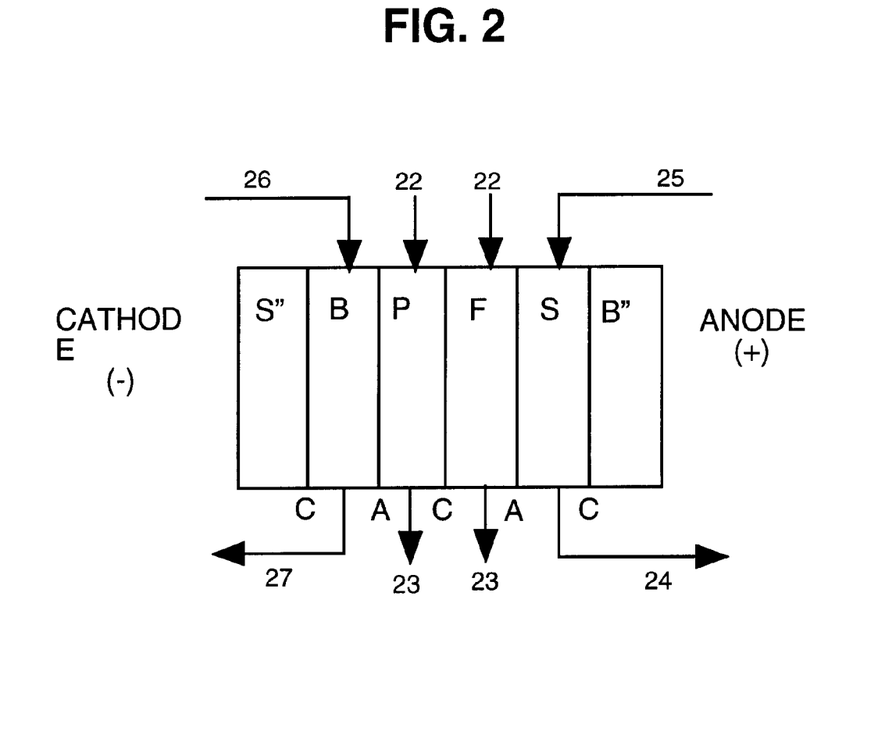
FIG. 2 illustrates a process flow diagram in accordance with the first variation of the present invention wherein a heat stable amine salt is converted into free base amine and a non-amine salt.

FIG. 2 (Four-Loop Mode)

Electrodialysis zone comprises a cathode compartment, an anode compartment and repeat units wherein each repeat unit contains a base compartment (B), a product compartment (P), a feed compartment (F), and a salt compartment (S). Also illustrated in electrodialysis zone are a base compartment (B") and a salt compartment (S") from adjacent repeat units. Electrodialysis zone contains cationic selective membranes (C) and anionic selective membranes (A). A direct current potential is passed transversely across each compartment in electrodialysis zone.

Amine solution is fed to the feed and product compartments via line 22 and returned to the gas treating process via line 23. Both the feed and product streams can be recirculated through a tank with make-up and bleed being lines 22 and 23 respectively. Alternatively the process could be operated in a batch mode.

A base such as caustic is circulated through the electrodialysis zone via lines 26 and 27. Salt solution is circulated in the electrodialysis zone via lines 24 and 25. Both the base solution and salt solution could be circulated on a once through basis, recirculated, or recirculated in a batch mode.

In the feed compartment (F), amine cations dissociate from the heat stable anions, such as chloride. The amine cations permeate through the cationic selective membrane to the product compartment. The heat stable anions such as chloride permeate though the anionic selective membrane to the salt compartment. In the base compartment (B), base anions such as hydroxide anions dissociate from the base cations such as sodium cations. The hydroxide anions permeate through the anionic selective membranes to the product compartment. In the product compartment the hydroxide anions combine with the protonated amine cations to form free base amine and water. In the base compartment the sodium cations permeates through the cationic selective membranes to the salt compartment. A water-containing stream is introduced into the salt compartment (S) and possibly into the product compartment. The later as an alternative to or in combination with an amine stream.

A product stream containing some amine in free base form in addition possibly with some amine heat stable salts, or at least a reduced concentration of heat stable amine salts or heat regenerable anions is discharged from the product compartment via line 23. It can be combined with the lean solvent stream 21 or alternatively with the rich solvent stream 29.

A salt product stream containing salts of heat stable anions such as sodium chloride is discharged from salt compartment (S) via line 24 and ultimately from the process via line 30.

The feed effluent stream having essentially the same composition as feedstream 22, except for a reduced level of heat stable amine salts, is discharged from feed compartment (F) via line 23. It can be combined with lean solvent in line 21 or rich solvent in line 29.

A base effluent stream having essentially the same composition as base stream 26, except for a lower concentration of base, is discharged from base compartment (B), via line 27. Base concentration in base stream 26 is controlled and adjusted by addition of base to the base recirculation tank 6, via line 28 (FIG. 1).

A solution of diethanolamine containing heat stable salts was treated in an electrodialysis stack. The operating conditions are given in Table 1. Solution conductivity and pH were measured. Feed stream conductivity dropped with time as the concentration of amine salts diminished. Base conductivity dropped with time, although it was increased from time to time by addition of caustic. Product pH increased as the concentration of free base amine increased. Conductivity remained essentially unchanged as the concentration of amine salts did not change significantly. Salt conductivity increased with time as the concentration salts in the solution increased.

Sulfate anion concentration in the feed stream decreased from 2.4% initially to 1.2% after 60 minutes of batch operation. Sulfate concentration in the salt stream increased from 1.4% initially to 2.5% after 60 minutes. The initial concentration in the salt solution was established in order to ensure sufficient conductivity for proper operation of the electrodialysis cell.

TABLE 1

| Time Min | Current (A) | Salt Cond. ($\mu$) | Product Cond. ($\mu$) | pH | Base Cond. ($\mu$) | pH | Feed Cond. ($\mu$) |
|---|---|---|---|---|---|---|---|
| 0 | 5 | 28000 | 30000 | 9.6 | 78000 | 12.8 | 30000 |
| 30 | 5.7 | 38000 | 31000 | 9.8 | 37000 | | 25000 |
| 60 | 5.8 | 53000 | 31000 | | 47000 | 12.4 | 19000 |

Figure 3:
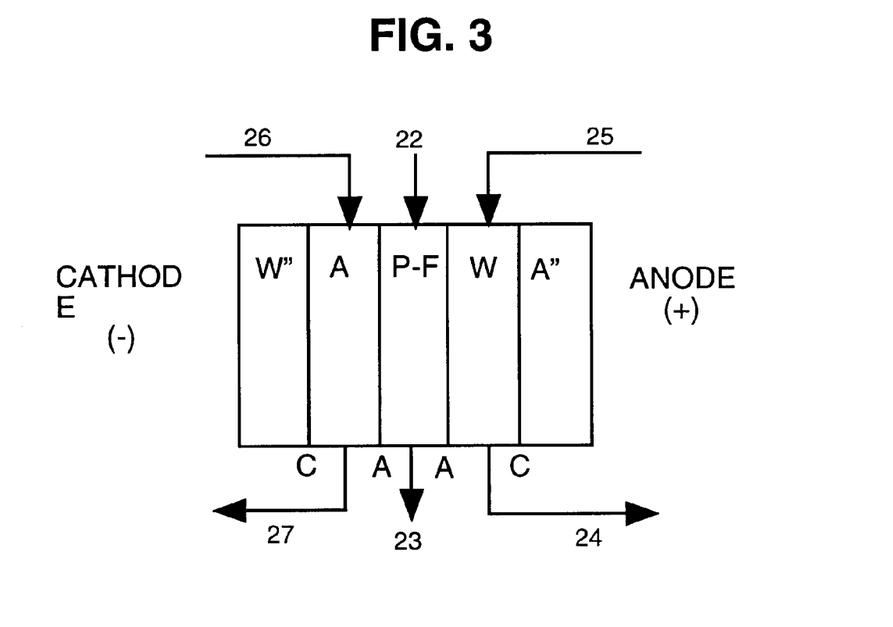
FIG. 3 illustrates a process flow diagram in accordance with the second variation of the present invention wherein a heat stable amine salt is converted into either the free base amine, or a regenerable amine salt and a non-amine salt.

FIG. 3 (Three Loop Mode)

Electrodialysis zone comprises a cathode compartment, an anode compartment and repeat units wherein each repeat unit contains a anion source compartment (A), a product-feed compartment (P-F), and a waste compartment (W). Also illustrated in electrodialysis zone are anion source compartment (A") and a waste compartment (W") from adjacent repeat units. If a source of regenerable anions if fed to the anion source compartment as an acid then an acid waste will be produced in the waste compartment instead of a salt solution. Electrodialysis zone contains cationic selective membranes (C) and anionic selective membranes (A). A direct current potential is passed traversely across each compartment in electrodialysis zone.

Amine solution is fed to the product-feed compartments via line 22 and returned to the gas treating process via line 23. Both the feed and product streams can be recirculated through a tank with make-up and bleed being lines 22 and 23 respectively. Alternatively the process could be operated in a batch mode or on a once through basis.

A base or a source of regenerable anions, such as caustic is circulated through the electrodialysis zone via lines 26 and 27. Salt or acid waste solution is circulated in the electrodialysis zone via lines 24 and 25. Both the anion source solution and waste solution could be circulated on a once through basis, recirculated or recirculated in a batch mode.

In the product-feed compartment (P-F), amine cations dissociate from the heat stable anions, such as chloride. The heat stable anions, such as chloride permeate though the anionic selective membrane to the waste compartment. In the anion source compartment (A), base anions such as hydroxide anions dissociate from the base cations such as sodium cations. The hydroxide anions permeate through the anionic selective membranes to the product-feed compartment. If a source of heat regenerable anions is used, such as sulfurous acid, sodium sulfite, sodium carbonate etc., the regenerable anions permeate through the anionic selective membrane to the product-feed compartment. In the product-feed compartment the hydroxide anions combine with the protonated amine cations to form free base amine and water. In the anion source compartment the sodium cations permeates through the cationic selective membranes to the waste compartment. A water-containing stream is introduced into the waste compartment (W).

A product-feed stream containing some amine in free base form in addition possibly with some amine heat stable salts, or at least a reduced concentration of heat stable and heat regenerable anions is discharged from the product compartment via line 23. It can be combined with the lean solvent stream 21 or alternatively with the rich solvent stream 29.

A waste product stream containing salts of heat stable anions such as sodium chloride is discharged from salt compartment (S) via line 24 and ultimately from the process via line 30.

An anion effluent stream having essentially the same composition as anion stream 26, except for a lower concentration of anions, is discharged from anion source compartment (A), via line 27. Anion concentration in anion stream 26 is controlled and adjusted by addition of anions to the anion source recirculation tank 6, via line 28 (FIG. 1).

Although the invention has been described with respect to specific aspects, those skilled in the art will recognize that other variations are possible within the scope of claims that follow. Those skilled in the art know that electrode rinse solutions are often passed through the anode and cathode compartments to supply anions and cations for electrical conductivity. In the present invention a portion of the base stream can be used for this purpose.

FIG. 4

Electrodialysis zone comprises a cathode compartment, an anode compartment and repeat units wherein each repeat unit contains a product-feed compartment (P-F), and a waste compartment (w). Also illustrated in electrodialysis zone are product-feed compartments (P-F") and a waste compartment (W") from adjacent repeat units. Electrodialysis zone contains bi-polar-membranes (BP) and anionic selective membranes (A). A direct current potential is passed traversely across each compartment in electrodialysis zone.

Amine solution is fed to the product-feed compartments via line 22 and returned to the gas treating process via line 23. Both the feed and product streams can be recirculated through a tank with make-up and bleed being lines 22 and 23 respectively. Alternatively the process could be operated in a batch mode or on a once through basis.

In the product-feed compartment (P-F), amine cations dissociate from the heat stable anions, such as chloride. The heat stable anions, such as chloride permeate though the anionic selective membrane to the waste compartment. Hydroxide anions are generated in the bi-polar membranes and permeate into the product-feed compartment. In the product-feed compartment the hydroxide anions combine with the protonated amine cations to form free base amine and water. Protons are also generated in the bi-polar membranes and permeate into the waste compartment (W). A water-containing stream is introduced into the waste compartment (W).

A product-feed stream containing some amine in free base form in addition possibly with some amine heat stable salts, or at least a reduced concentration of heat stable and heat regenerable anions is discharged from the product compartment via line 23. It can be combined with the lean solvent stream 21 or alternatively with the rich solvent stream 29.

A waste product stream containing acids of heat stable anions such as hydrochloric acid is discharged from waste compartment (W) via line 24 and ultimately from the process via line 30.

Although the invention has been described with respect to specific aspects, those skilled in the art will recognize that other variations are possible within the scope of claims that follow. Those skilled in the art know that electrode rinse solutions are often passed through the anode and cathode compartments to supply anions and cations for electrical conductivity. In the present invention a portion of the waste stream or a dedicated stream can be used for this purpose.

What is claimed is:

1. A process for removing heat-stable amine salts from a contaminated aqueous amine solution, comprising
    (a) passing a feedstream comprising an amine in salt form having heat stable amine anions associated therewith to an electrodialysis zone having a cathode compartment, an anode compartment and at least one repeat unit comprising a base compartment disposed between the cathode compartment and the anode compartment, a product compartment disposed between the base compartment and an anode compartment, a feed compartment disposed between the product compartment and the anode compartment and the salt compartment disposed between the feed compartment and the anode compartment, said feed stream being passed to the feed compartment;
    (b) passing a base stream comprising a base to the base compartment;
    (c) passing a direct current potential transversely across each compartment, said current being effective to cause (1) amine cations to dissociate from the heat stable amine salts in the feed compartment and pass into the product compartment;(2) base anions to dissociate from the base in the base compartment and pass into the product compartment; (3) heat stable anions to dissociate from the heat stable amine salts in the feed compartment and pass into the salt compartment; and
    (d) discharging from the product compartment a product stream comprising at least in part an amine in free base form in which the level of heat stable amine salts and/or non heat stable amine salts has been lowered.

2. The process of claim 1 wherein the feedstream further comprises water and the amine in free base form.

3. The process of claim 1 further comprising discharging a feed effluent stream from the feed compartment and recycling at least a portion of the feed effluent stream to the feed compartment.

4. The process of claim 1 further comprising discharging a salt effluent stream from the waste compartment and recycling at least a portion of the salt stream to the waste compartment.

5. The process of claim 1 wherein the base is selected from the group consisting of alkali metal oxides, alkali metal hydroxides, alkaline earth oxides, alkaline earth hydroxides, metal oxides and metal hydroxides.

6. The process of claim 5 further comprising discharging a waste effluent stream from the waste compartment and recycling at least a portion of the waste stream to the waste compartment.

7. The process of claim 5 wherein the source of regenerable anions is comprised of acids of heat regenerable anions.

8. The process of claim 5 wherein the source or regenerable anions is selected from a group consisting of alkali metal and alkali earth salts in which the anions are heat regenerable.

9. The process of claim 8 wherein the feedstream further comprises water and the amine in free base form.

10. The process of claim 8 further comprising discharging a product-feed effluent stream from the feed compartment and recycling at least a portion of the product-feed effluent stream to the feed compartment.

11. The process of claim 8 further comprising discharging a waste effluent stream from the waste compartment and recycling at least a portion of the waste stream to the waste compartment.

12. A process for removing heat-stable amine salts from a contaminated aqueous amine solution, comprising
    (a) passing a feedstream comprising an amine in salt form having heat stable amine anions associated therewith to an electrodialysis zone having a cathode compartment, an anode compartment and at least one repeat unit comprising an anion source compartment disposed between the cathode compartment and the anode compartment, a product-feed compartment disposed between the anion source compartment and the anode compartment and a waste compartment disposed between the product-feed compartment and an anode compartment, said feed stream being passed to the product-feed compartment;
    (b) passing a anion source stream comprising a base or a source of regenerable anions in either salt or acid form to the anion source compartment.
    (c) passing a direct current potential transversely across each compartment, said current being effective to cause (1) amine cations to dissociate from the heat stable amine salts in the feed compartment;(2) base anions or regenerable anions to dissociate in the anion source compartment and pass into the product compartment; (3) heat stable anions to dissociate from the heat stable amine salts in the product-feed compartment and pass into the waste compartment; and
    (d) discharging from the product-feed compartment a product stream comprising at least in part an amine in free base form or in a regenerable form in which the level of heat stable amine salts has been lowered.

13. The process of claim 12 wherein the feedstream further comprises water and the amine in free base form.

14. The process of claim 12 further comprising discharging a product-feed effluent stream from the product-feed compartment and recycling at least a portion of the product-feed effluent stream to the feed compartment.

15. The process of claim 12 wherein the base is selected from the group consisting of alkali metal oxides, alkali metal hydroxides, alkaline earth oxides, alkaline earth hydroxides, metal oxides and metal hydroxides.

16. A process for removing heat-stable amine salts from a contaminated aqueous amine solution, comprising
    (a) passing a feedstream comprising an amine in salt form having heat stable amine anions associated therewith to an electrodialysis zone having a cathode compartment, an anode compartment and at least one repeat unit comprising a product-feed compartment disposed between the cathode compartment and the anode compartment and a waste compartment disposed between the product-feed compartment and an anode compartment, said feed stream being passed to the product-feed compartment;.
    (b) passing a direct current potential transversely across each compartment, said current being effective to cause (1) amine cations to dissociate from the heat stable amine salts in the product-feed compartment;(2) hydroxyl anions to be generated in the bi-polar membranes and pass into the product-feed compartment, (3) heat stable anions to dissociate from the heat stable amine salts in the product-feed compartment and pass into the salt compartment, (4) protons to be generated in the bi-polar membranes and pass into the waste compartment and
    (d) discharging from the product-feed compartment a product stream comprising at least in part an amine in free base form in which the level of heat stable amine salts and/or non heat stable amine salts has been lowered.

* * * * *